(12) United States Patent
Gadelrab et al.

(10) Patent No.: US 10,961,563 B1
(45) Date of Patent: Mar. 30, 2021

(54) NANOSCALE TOPOGRAPHY SYSTEM FOR USE IN DNA SEQUENCING AND METHOD FOR FABRICATION THEREOF

(71) Applicant: Robert Bosch GmbH, Stuttgart (DE)

(72) Inventors: Karim Gadelrab, Boston, MA (US); Giovanna Bucci, Santa Clara, CA (US); Nathan Craig, Santa Clara, CA (US); Christopher Johnson, San Carlos, CA (US); Nadezda Fomina, Redwood City, CA (US); Young Shik Shin, Mountain View, CA (US)

(73) Assignee: Robert Bosch GmbH, Stuttgart (DE)

( * ) Notice: Subject to any disclaimer, the term of this patent is extended or adjusted under 35 U.S.C. 154(b) by 0 days.

(21) Appl. No.: 16/721,318

(22) Filed: Dec. 19, 2019

(51) Int. Cl.
| | |
|---|---|
| *C12Q 1/00* | (2006.01) |
| *B01L 3/00* | (2006.01) |
| *C12Q 1/6806* | (2018.01) |
| *G01N 1/28* | (2006.01) |
| *B82B 3/00* | (2006.01) |
| *B82B 1/00* | (2006.01) |

(52) U.S. Cl.
CPC ............ *C12Q 1/6806* (2013.01); *B82B 1/001* (2013.01); *B82B 3/0019* (2013.01); *G01N 1/286* (2013.01)

(58) Field of Classification Search
None
See application file for complete search history.

(56) References Cited

U.S. PATENT DOCUMENTS

| | | | |
|---|---|---|---|
| 8,722,327 | B2 | 5/2014 | Cao et al. |
| 9,568,464 | B2 | 2/2017 | Van Der Zaag et al. |
| 10,253,362 | B2 | 4/2019 | Yoshida et al. |
| 2004/0033515 | A1* | 2/2004 | Cao ................ G03F 7/2008 435/6.12 |
| 2004/0197843 | A1* | 10/2004 | Chou ................ G01N 21/648 435/7.92 |
| 2006/0011862 | A1* | 1/2006 | Bernstein .......... B01L 3/502761 250/461.2 |

(Continued)

OTHER PUBLICATIONS

Bai et al., "Perpendicular Block Copolymer Microdomains in High Aspect Ratio Templates", Nano Letters, 2015 American Chemical Society, Sep. 21, 2015, pp. 6901-6908.

(Continued)

*Primary Examiner* — Nathan A Bowers
(74) *Attorney, Agent, or Firm* — Brooks Kushman P.C.

(57) ABSTRACT

A method of fabricating a nanoscale topography system for inducing unfolding of a DNA molecule for sequencing includes providing a substrate and creating trench walls on the substrate which define a trench therebetween. The method further includes depositing a layer of a block copolymer (BCP) in the trench and forming cylindrical domains by self-assembly of the BCP between the trench walls, removing a first portion of the cylindrical domains to create a vacant region in the trench, and depositing a subsequent layer of the BCP in the vacant region and forming spherical domains by self-assembly of the BCP between the trench walls adjacent a second portion of the cylindrical domains. The spherical domains form staggered post structures for unfolding the DNA molecule and the cylindrical domains form parallel channel structures for entry of the DNA molecule for sequencing.

20 Claims, 3 Drawing Sheets

(56) References Cited

U.S. PATENT DOCUMENTS

| 2015/0027980 | A1* | 1/2015 | Van Der Zaag | B82Y 30/00 216/17 |
|---|---|---|---|---|
| 2016/0244823 | A1* | 8/2016 | Yoshida | C12Q 1/6872 |
| 2017/0212098 | A1* | 7/2017 | Stolovitzky | B01L 3/502715 |
| 2018/0157790 | A1* | 6/2018 | Smolyanitsky | C12Q 1/6806 |

OTHER PUBLICATIONS

Bates et al., "50th Anniversary Perspective: Block Polymers—Pure Potential", 2016 American Chemical Society, Dec. 31, 2016, Macromolecules 2017, pp. 3-22.

Cheng et al., "Nanostructure engineering by templated self-assembly of block copolymers", 2004 Nature Publishing Group, vol. 3, Nov. 2004, pp. 823-828.

Do et al., "Directed self-assembly of a two-state block copolymer system", Nano Convergence, 2018, 9 pages.

Reisner et al., "DNA confinement in nanochannels: physics and biological applications", Rep. Prog. Phys., 75, Sep. 13, 2012, 35 pages.

Douville et al., "DNA Linearization through confinement in nanofluidic channels", Anal Bioanal Chem, 2008, pp. 2395-2409.

Chan et al., "DNA Mapping Using Microfluidic Stretching and Single-Molecule Detection of Fluorescent Site-Specific Tags", Genome Research, 2004 Cold Spring Harbor Laboratory, pp. 1137-1146.

Michalet et al., "Dynamic Molecular Combing: Stretching the Whole Human Genome for High-Resolution Studies", Science, vol. 277, Sep. 1997, pp. 1518-1523.

Cheng et al., "Fabrication of nanostructures with long-range order using block copolymer lithography", Applied Physics Letters, vol. 81, No. 19, Nov. 4, 2002, pp. 3657-3659.

Wang et al., "Hydrodynamics of Diamond-Shaped Gradient Nanopillar Arrays for Effective DNA Translocation into Nanochannels", 2015 American Chemical Society, vol. 9, No. 2, pp. 1206-1218.

Gadelrab et al., "Inverting the design path for self-assembled block copolymers", The Royal Society of Chemistry, Mol. Syst. Des. Eng., 2017, pp. 539-548.

Mantere et al., "Long-Read Sequencing Emerging in Medical Genetics", Frontiers in Genetics, May 2019, vol. 10, Article 426, 14 pages.

Menard et al., "Electrokinetically-Driven Transport of DNA through Focused Ion Beam Milled Nanofluidic Channels", 2012 American Chemical Society, Anal. Chem., vol. 85, pp. 1146-1153.

Tavakkoli et al., "Multilayer block copolymer meshes by orthogonal self-assembly", Nature Communications, Jan. 22, 2016, 10 pages.

Eid et al., "Real-Time DNA Sequencing from Single Polymerase Molecules", Science, vol. 323, Jan. 2, 2009. pp. 133-138.

Cheng et al., "Templated Self-Assembly of a PS-Branch-PDMS Bottlebrush Copolymer", Nano Letters, 2018 American Chemical Society, Jun. 7, 2018, pp. 4360-4369.

Gadelrab et al., "Limits of Directed Self-Assembly in Block Copolymers", Nano Letters, 2018 American Chemical Society, May 18, 2018, pp. 3766-3772.

Jeong et al., "Directed self-assembly of block copolymers for next generation nanolithography", Materials Today, vol. 16, No. 12, Dec. 2013, pp. 469-476.

* cited by examiner

NANOSCALE TOPOGRAPHY SYSTEM FOR USE IN DNA SEQUENCING AND METHOD FOR FABRICATION THEREOF

TECHNICAL FIELD

Embodiments relate to a nanoscale topography system for use in DNA sequencing and a method of fabricating the nanoscale topography system.

BACKGROUND

DNA is the central storage unit of genetic information, and extracting this information is one major goal in the field of biology. Through gene sequencing, insights into genome variation, genetic mutation and replication dynamics can be achieved. Sequencing technology has made enormous strides over the past decades in reading genetic information; however, the vision of extracting the genetic code directly from a single long DNA molecule out of a single cell has still met with limited success. While human DNA has billions of base pairs, the direct read of base pair sequences is hindered by the complex compactification of DNA inside the cell. Hence, the folding and twisting of the soft condensed matter of DNA has to be unraveled to access the genetic sequence.

Due to the extreme length of DNA (human chromosome of 250 million base pairs has a full stretched length of ~8.5 cm), the DNA is first sheared or enzymatically digested into fragments of a maximum length of few millimeters and incorporated into bacterial or yeast artificial chromosomes. Libraries of fragments of ~1000 base pairs can be directly sequenced and analyzed.

DNA linearization plays a crucial role in gene sequencing. Different techniques rely on hydrodynamic forces to achieve DNA extension. One attractive example is molecular combing. There, a salinized coverslip is lowered into a reservoir containing DNA. During the coverslip residence time inside the reservoir, one or both ends of DNA are attached to the coverslip surface. The coverslip is slowly withdrawn from the surface where an air-liquid meniscus is formed. The capillary forces will stretch the DNA molecule. The technique is fast and relatively simple; however, it does not allow for reliable manipulation of DNA fragments longer than a few hundred microns.

More recently, Chan et al. (Genome Res. 14, 1137-1146 (2004)) proposed using direct linear analysis (DLA) to analyze DNA. The random coil conformation of DNA is unwound and stretched using hydrodynamic forces generated in laminar flow by a tapered microfluidic channel. In this setup, the solution is injected into the loading port and the sample solution is pressure driven into the chip, and tagged DNA molecules travel with the flow in their random-coil forms. Downstream, DNA uncoils as it interacts with the post fields. These pre-stretched molecules stretch to completion under hydrodynamic influences in the tapered region. The short taper length produces flow acceleration over a distance comparable to the size of the DNA. The resulting differences in flow velocities around different parts of the molecule produce the force that stretches it.

However, this large size topography proved to have limited efficacy in extending DNA molecules, as the achieved extension is typically reverted in the gaps preceding the nano-channels. The real potential of single molecule sequencing requires orders of magnitude of miniaturization of topography (from micro to nano channels and posts), bringing new challenges in addressing nanoscale forces, complexity of nano-fabrication, and the cost of devices.

Nanoscale topography can be achieved using sophisticated techniques that vary in accuracy, cost, and throughput. For example, electron beam (e-beam) lithography is a process using a focused beam of electrons to chemically alter a resist via energy loss through ionization. The feature resolution is limited to critical dimensions of approximately 3 nm due to scattering in the resist. E-beam lithography is often used for the fabrication of nanochannels and pores given its impressive resolution, though it is a time-consuming and expensive technique not well suited for exposing large areas across an entire wafer.

Focused ion beam (FIB) lithography, whereby a focused beam of ions (typically Ga) physically sputter neutral and ionized substrate atoms upon impact, has also been used to fabricate nanochannels. This method is quite versatile since it can be used to etch, image, and deposit films in conjunction with precursor gases (similarly to chemical vapor deposition). However, it is more useful for prototyping than for patterning large areas.

Nanoimprint lithography can potentially address the requirement of high throughput fabrication. There, a carefully designed inverse template/mold is fabricated using e-beam lithography or other high-resolution techniques. The template is pressed against a thin resist that is heated above its glass transition temperature. The resist is then cooled and the mold is removed. The uneven resist surface is then exposed to directional etching where the thin regions are removed faster than the thick regions, creating channels. The mold can be used several times to create multiple channels on multiple surfaces. Nonetheless, mold erosion and flow behavior of the resist under compression negatively impact reaching small feature size.

SUMMARY

In one or more embodiments, a method of fabricating a nanoscale topography system for inducing unfolding of a DNA molecule for sequencing includes providing a substrate and creating trench walls on the substrate which define a trench therebetween. The method further includes depositing a layer of a block copolymer (BCP) in the trench and forming cylindrical domains by self-assembly of the BCP between the trench walls, removing a first portion of the cylindrical domains to create a vacant region in the trench, and depositing a subsequent layer of the BCP in the vacant region and forming spherical domains by self-assembly of the BCP between the trench walls adjacent a second portion of the cylindrical domains. The spherical domains form staggered post structures for unfolding the DNA molecule and the cylindrical domains form parallel channel structures for entry of the DNA molecule for sequencing.

In one or more embodiments, a method of fabricating a nanoscale topography system for inducing unfolding of a DNA molecule for sequencing includes providing a substrate and creating trench walls on the substrate which define a trench therebetween. The method further includes depositing a layer of a block copolymer (BCP) in the trench and forming cylindrical domains by self-assembly of the BCP between the trench walls, wherein the BCP comprises polystyrene-b-polydimethylsiloxane (PS-b-PDMS). The method further includes removing a first portion of the cylindrical domains to create a vacant region in the trench, depositing a subsequent layer of the BCP in the vacant region and forming spherical domains by self-assembly of the BCP between the trench walls adjacent a second portion of the cylindrical domains, and providing surface functionalization of at least one of the trench and the trench walls to control positioning and orientation of the cylindrical and spherical domains, wherein surface functionalization is preferential to a majority block of the BCP. The spherical domains form staggered post structures for unfolding the DNA molecule and the cylindrical domains form parallel channel structures for entry of the DNA molecule for sequencing.

In one or more embodiments, a nanoscale topography system for inducing unfolding of a DNA molecule for sequencing includes a substrate and trench walls on the substrate which define a trench therebetween. The system further includes a layer of a block copolymer (BCP) deposited in the trench which self-assembles to form cylindrical domains between the trench walls, a vacant region in the trench formed by removing a first portion of the cylindrical domains, and a subsequent layer of the BCP deposited in the vacant region which self-assembles to form spherical domains between the trench walls adjacent a second portion of the cylindrical domains. The spherical domains form staggered post structures for unfolding the DNA molecule and the cylindrical domains form parallel channel structures for entry of the DNA molecule for sequencing.

In one or more embodiments, the BCP comprises polystyrene-b-polydimethylsiloxane (PS-b-PDMS).

In one or more embodiments, the cylindrical domains include a plurality of in-plane cylinders.

In one or more embodiments, creating the trench walls includes depositing an antireflective coating (ARC) layer on the substrate, depositing a silica layer on the ARC layer, and depositing a photoresist layer on the silica layer.

In one or more embodiments, creating the trench walls further includes producing a photoresist grating, and removing the silica layer and the ARC layer.

In one or more embodiments, surface functionalization of at least one of the trench and the trench walls is used to control positioning and orientation of the cylindrical and spherical domains.

In one or more embodiments, surface functionalization is preferential to a majority block of the BCP.

In one or more embodiments, forming the cylindrical domains includes annealing the layer of the BCP to facilitate self-assembly, and etching the layer of the BCP to reveal the cylindrical domains.

In one or more embodiments, removing the first portion of the cylindrical domains includes depositing a photoresist to cover the second portion of the cylindrical domains and removing the first portion of the cylindrical domains via etching.

In one or more embodiments, forming the spherical domains includes annealing the subsequent layer of the BCP to facilitate self-assembly, and etching the subsequent layer of the BCP to reveal the spherical domains.

In one or more embodiments, the method includes transferring a combined structure of the cylindrical domains and the spherical domains to the substrate.

In one or more embodiments, etching the layer of the BCP includes removing a PDMS top coat and a PS matrix of the layer to leave behind a plurality of in-plane PDMS cylinders, and etching the subsequent layer of the BCP includes removing a PDMS top coat and a PS matrix of the subsequent layer to leave behind a plurality of PDMS spherical domains.

In one or more embodiments, the substrate includes sensing electrodes.

DETAILED DESCRIPTION

As required, detailed embodiments of the present invention are disclosed herein; however, it is to be understood that the disclosed embodiments are merely exemplary of the invention that may be embodied in various and alternative forms. The figures are not necessarily to scale; some features may be exaggerated or minimized to show details of particular components. Therefore, specific structural and functional details disclosed herein are not to be interpreted as limiting, but merely as a representative basis for teaching one skilled in the art to variously employ the present invention.

Except in the examples, or where otherwise expressly indicated, all numerical quantities in this description indicating amounts of material or conditions of reaction and/or use are to be understood as modified by the word "about". The first definition of an acronym or other abbreviation applies to all subsequent uses herein of the same abbreviation and applies mutatis mutandis to normal grammatical variations of the initially defined abbreviation; and, unless expressly stated to the contrary, measurement of a property is determined by the same technique as previously or later referenced for the same property.

Unless indicated otherwise, all technical and scientific terms used herein have the same meaning as commonly understood by one of ordinary skill in the art to which the present disclosure belongs.

It is also to be understood that this disclosure is not limited to the specific embodiments and methods described below, as specific components and/or conditions may, of course, vary. Furthermore, the terminology used herein is used only for describing particular embodiments and is not intended to be limiting in any way.

It must also be noted that, as used in the specification and the appended claims, the singular form "a," "an," and "the" comprise plural referents unless the context clearly indicates otherwise. For example, reference to a component in the singular is intended to comprise a plurality of components.

The terms "or" and "and" can be used interchangeably and can be understood to mean "and/or".

The term "comprising" is synonymous with "including," "having," "containing," or "characterized by." These terms are inclusive and open-ended and do not exclude additional, unrecited elements or method steps.

The phrase "consisting of" excludes any element, step, or ingredient not specified in the claim. When this phrase appears in a clause of the body of a claim, rather than immediately following the preamble, it limits only the element set forth in that clause; other elements are not excluded from the claim as a whole.

The phrase "consisting essentially of" limits the scope of a claim to the specified materials or steps, plus those that do not materially affect the basic and novel characteristic(s) of the claimed subject matter.

The terms "comprising", "consisting of", and "consisting essentially of" can be alternatively used. When one of these three terms is used, the presently disclosed and claimed subject matter can include the use of either of the other two terms.

Unless expressly stated to the contrary: percent, "parts of," and ratio values are by weight; the description of a group or class of materials as suitable or preferred for a given purpose in connection with the disclosure implies that mixtures of any two or more of the members of the group or class are equally suitable or preferred; description of constituents in chemical terms refers to the constituents at the time of addition to any combination specified in the description, and does not necessarily preclude chemical interactions among the constituents of a mixture once mixed.

It should also be appreciated that integer ranges explicitly include all intervening integers. For example, the integer range 1-10 explicitly includes 1, 2, 3, 4, 5, 6, 7, 8, 9, and 10. Similarly, the range 1 to 100 includes 1, 2, 3, 4 . . . 97, 98, 99, 100. Similarly, when any range is called for, intervening numbers that are increments of the difference between the upper limit and the lower limit divided by 10 can be taken as alternative upper or lower limits. For example, if the range is 1.1. to 2.1 the following numbers 1.2, 1.3, 1.4, 1.5, 1.6, 1.7, 1.8, 1.9, and 2.0 can be selected as lower or upper limits.

In the examples set forth herein, concentrations, temperature, and reaction conditions (e.g., pressure, pH, flow rates, etc.) can be practiced with plus or minus 50 percent of the values indicated rounded to or truncated to two significant figures of the value provided in the examples. In a refinement, concentrations, temperature, and reaction conditions (e.g., pressure, pH, flow rates, etc.) can be practiced with plus or minus 30 percent of the values indicated rounded to or truncated to two significant figures of the value provided in the examples. In another refinement, concentrations, temperature, and reaction conditions (e.g., pressure, pH, flow rates, etc.) can be practiced with plus or minus 10 percent of the values indicated rounded to or truncated to two significant figures of the value provided in the examples.

Throughout this application, where publications are referenced, the disclosures of these publications in their entireties are hereby incorporated by reference into this application to more fully describe the state of the art to which this disclosure pertains.

Next generation sequencing of DNA requires nanoscale control over DNA. The native folded form of the DNA chain needs to be unraveled for the access to each individual base to precisely decode genetic information stored in the molecule. A promising way of achieving DNA unwinding is to force the DNA through a grid of posts with gaps smaller than the unconstrained size of the molecule before accessing a sensing zone. The full potential of such a method requires an efficient fabrication technique to create a nanoscale topography system of posts and channels.

The inherent pattern of self-assembled block copolymers (BCPs) provides access to such intricate structures on a length scale of 10-100 nm, controlled by molecular chemistry and materials processing conditions (depositing/spin-coating, annealing, and etching). In particular, directed self-assembly of a monolayer of BCPs minimizes defects, improves long-range order, and guides the formation of the periodic lines and dots generated by BCPs microphase separation. The implementation of directed self-assembly of BCPs in fabricating DNA sequencing devices addresses many of the technological challenges in a relatively simple and cost-efficient way.

Accordingly, disclosed herein is a fabrication method of creating a nanoscale topography system to induce DNA unfolding for the purpose of DNA sequencing. The fabrication method uses BCPs as a masking technique to etch post and channel topography into substrates. The innate capability of BCPs to self-assemble into periodic patterns creates uniform domain sizes with controllable spacing, where the pattern of repeating domains and domain spacing are controlled using polymer chemistry and polymer processing. The method employs directed self-assembly of BCPs as an inexpensive and fast approach of creating periodic nanoscale patterns with good long-range order.

BCPs are a special category of soft matter where the polymeric chain contains more than one chemistry gathered in blocks. In its simplest form, a linear diblock copolymer resembles two polymeric chains connected at one end. The limited miscibility of the constituent polymers in each block promotes phase separation that reduces interfacial contact between the blocks, while the arrangement of different blocks within the same molecule limits the extent of the spatial separation resulting in a periodic pattern rather than macroscale phase separation. The spontaneous microphase separation of BCPs typically produces regions (grains) of microdomains with short range order resembling a polycrystalline structure, each grain having a different orientation and localized defects. However, better control over BCP order can be achieved using a guiding chemical and/or topographical template formed on the substrate, which is the process known as directed self-assembly (DSA). Defect elimination and pattern alignment are defined by the template based on factors such as preferential surface wetting and the commensurability between the BCP period and the size of the template.

Among the different chemistries used in diblock copolymers, polystyrene-b-polydimethylsiloxane (PS-b-PDMS) shows great promise for nanoscale applications. The large degree of incompatibility between the two blocks promotes phase separation with a sharp interface. In addition, the process of revealing the polymer domains involves oxygen plasma which burns away the carbon-based PS and transforms the silicon-based PDMS into silica, creating a very stable glass pattern that can be used as a mask to etch the nanopattern into a substrate. PS-b-PDMS can produce different domain shapes (spheres, cylinders, lamellae) depending on the proportion of its constituents.

One difficulty that has typically been encountered with PS-b-PDMS is the migration of PDMS to the top free surface due the low surface energy of PDMS compared to PS. This behavior generates in-plane motifs that render the lamellar structure to be of limited use for nanoscale patterning (standing lamellae can be etched to the substrate, but lying down sheets cover the entire substrate with no visible pattern). Hence, only spherical and cylindrical domains can be used as masks. To control domain positioning and orientation, a one-dimensional confinement using trenches is implemented herein.

Although PS-b-PDMS is described herein in connection with the disclosed fabrication method, it is understood that pattern formation through microphase separation is a general property of BCPs and, as such, different combinations of BCP chemistries could alternatively be employed. Accordingly, BCP can be of any incompatible chemistries (e.g., PS-PDMS, PS-PMMA, PS-P4VP etc.), however, PS-PDMS is expected to perform well at smaller length scale due to high blocks incompatibility. Should other chemistries be utilized, they should still have the polymer interface and stability of the final pattern necessary for targeting smaller features.

With reference to FIGS. 1-4, the following fabrication steps may be used to create a nanoscale topographic system 10 with entry posts 12 and a plurality of parallel channels 14 for inducing unfolding of a DNA molecule for sequencing according to one or more embodiments. The method may be divided into three general parts: template fabrication, cylinder forming BCP self-assembly, and sphere forming BCP self-assembly. The schematic drawings show the sequence of fabrication steps which may be used to realize a post/channel system using a BCP self-assembled pattern as a mask.

Figure 1:
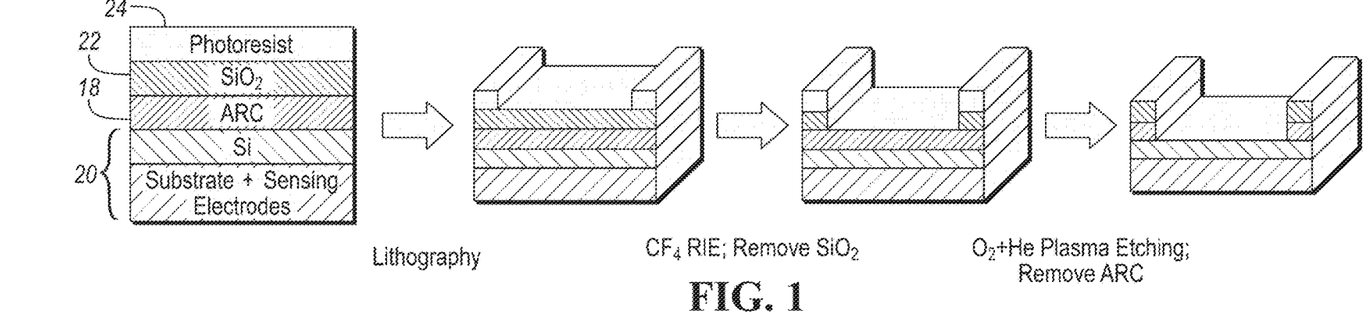
FIG. 1 is a schematic illustration showing template fabrication for a nanoscale topography system according to one or more embodiments.

Referring to FIG. 1, template fabrication according to one or more embodiments aims at creating an extended trench 16 with a width of approximately, but not limited to, 200 nm. First, an antireflective coating (ARC) layer 18 may be deposited, such as via spin coating, on a pre-patterned substrate 20 (e.g. Si) with sensing electrodes and then heated to induce cross-linking. Next, a silica layer 22 ($SiO_2$) may be deposited, such as via electron beam evaporation. A photoresist 24 may then be deposited (e.g., spin coated) on top of the silica layer 22 and heated. Using lithography, the sample may be exposed by a laser-generated interference pattern, and post-exposure development may be used to produce a photoresist grating. Next, reactive-ion (e.g. $CF_4$ plasma) etching may be used to remove the silica layer 22 (transfer the photoresist pattern into the silica layer 22), and then $O_2$+He plasma etching may be used to remove the ARC layer 18 (transfer the pattern into the ARC layer 18) to make stable trench walls 26 to guide the self-assembly of BCPs. Trench walls 26 are used to direct the self-assembly of the post 12/channel 14 pattern, control channel 14 orientation, and bring the posts 12 and channels 14 into close proximity, as described further below.

Next, the fabrication steps to create a topographic pattern for DNA unfolding are described. According to one or more embodiments, the application of BCPs in the trench 16 between the trench walls 26 may follow a sequence of steps of depositing, annealing, and etching.

Figure 2:
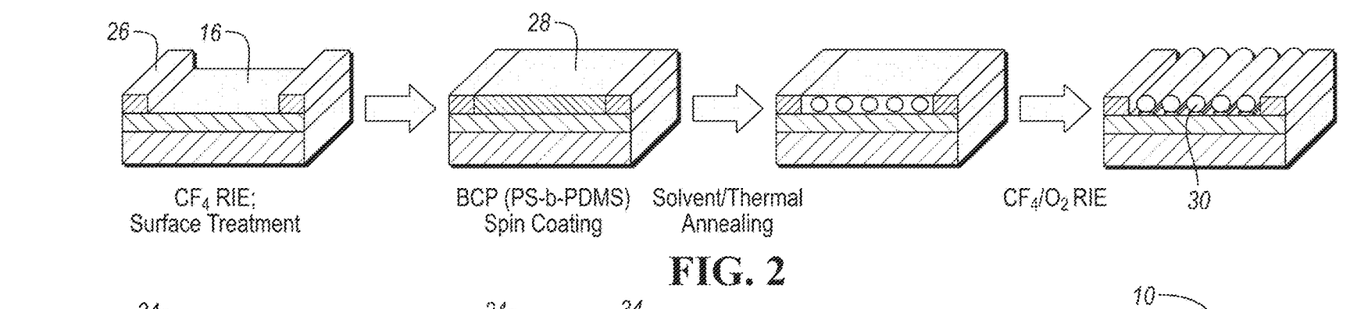
FIG. 2 is a schematic illustration showing various steps of directed self-assembly of cylinder-forming block copolymers for fabricating the nanoscale topography system.

Turning to FIG. 2, surface functionalization of the trench 16 and/or the trench walls 26 may first be employed to improve BCP wetting and to improve overall order. In particular, BCP in-plane cylinders have the natural tendency to align orthogonal to trench walls 26. To promote parallel orientation of cylinders, surface functionalization to be preferential to the majority block (e.g. PS) may be utilized. Surface functionalization may include depositing (e.g. spin coating) the majority block onto the trench 16 and/or trench walls 26, thermally annealing, and rinsing to remove any ungrafted brush polymer.

With continuing reference to FIG. 2, directed self-assembly of cylinder-forming BCP is illustrated. A layer 28 of BCP (e.g. PS-b-PDMS) is deposited (e.g. spin coated) in the trench 16 to a thickness which results in a monolayer of in-plane cylinders. Next, an annealing process is used to facilitate self-assembly. This can be achieved either thermally or by solvent annealing in an atmosphere of solvents. Etching, such as reactive-ion etching (RIE), may then be used to remove the PDMS top-coat and PS matrix of the BCP monolayer 28 to leave behind oxidized, in-plane PDMS cylinders 30. In particular, $CF_4$ may be used to remove the layer of PDMS that forms at the top of the BCP film, and $O_2$ may be used to remove the PS matrix. By revealing the BCP structure, a series of parallel cylinders 30 inside the trench 16 are obtained. Accordingly, channel structures 14 are generated by a monolayer of in-plane cylinders 30. Alternatively, channel structures 14 could be generated by a template of vertically standing lamellae.

Figure 3:
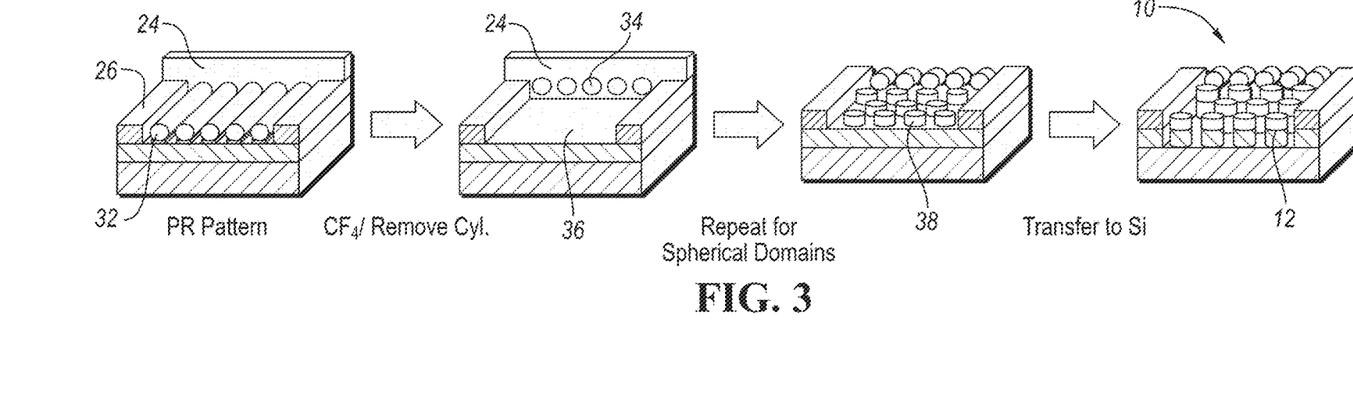
FIG. 3 is a schematic illustration showing various steps of directed self-assembly of sphere-forming block copolymers for fabricating the nanoscale topography system.

FIG. 3 illustrates the directed self-assembly of sphere-forming BCP. In order to position posts 12 in the vicinity of the in-plane cylinders 30, a first portion 32 of the cylinders 30 may be removed. In one or more embodiments, a photoresist 24 may be applied and patterned to cover the trench 16 and a second portion 34 of the in-plane cylinders 30. The first portion 32 of the cylindrical domains 30 occupying the location desired for the posts 12 may then be removed, such as by using $CF_4$ etching. By doing so, a generally flat, vacant region 36 inside the trench 16 may be recovered in which to position the spherical domains 38.

Similar to those for creating cylindrical BCP 30, BCP fabrication steps are employed to create spherical domains 38 (e.g. hexagonal), including surface functionalization. A subsequent BCP layer (e.g. PS-b-PDMS) is deposited (e.g. spin coated) in the trench to a thickness which results in a monolayer of spherical domains. Next, an annealing process is used to facilitate self-assembly. This can be achieved either thermally or by solvent annealing in an atmosphere of solvents. Etching, such as reactive-ion etching (RIE), may then be used to remove the PDMS top-coat and PS matrix of the BCP monolayer to leave behind oxidized PDMS spherical domains 38. In particular, $CF_4$ may be used to remove the surface coating PDMS layer that forms at the top of the BCP film, and $O_2$ may be used to remove the PS matrix and to subsequently oxidize the PDMS block into amorphous silica. By revealing the BCP structure, a monolayer of spheres 38 inside the trench 16 is obtained which serve as post structures 12. Alternatively, post structures 12 could be generated by a template of vertically standing cylinders.

Referring again to FIG. 3, the combined structure of the in-plane cylinders 30 and spheres 38 may then be transferred to the silicon substrate 20, such as using RIE. According to one non-limiting embodiment, the final depth of silicon topography is in the same order of magnitude of half domain spacing of the in-plane cylinders. The BCP silica domains can be removed using $CF_4$ exposure. In one non-limiting embodiment, the post 12 spacing and channel 14 width is approximately ~10 nm.

Figure 4:
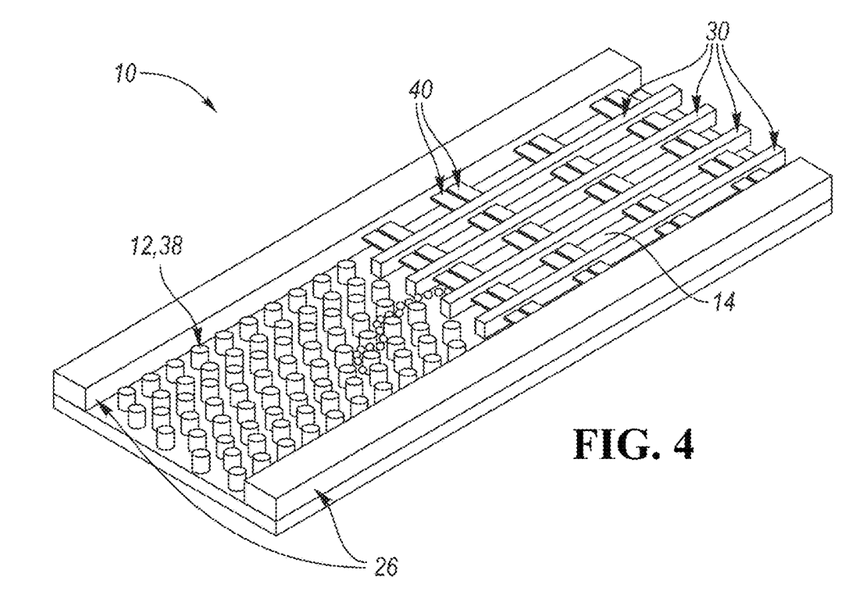
FIG. 4 is a schematic illustration of a nanoscale topography system for unfolding DNA (depicted as a series of beads entering the middle channel) according to one or more embodiments.

FIG. 4 shows a schematic of the final layout of a nanoscale topographic system 10 to be used to unfold DNA for sequencing according to one or more embodiments. As illustrated, the plurality of posts 12 causes the DNA to unfold or unwind as it is forced to pass through the staggered pattern towards the channels 14. The DNA molecule can enter any of the parallel channels 14 to be read by a series of sensing electrodes 40.

While hydrodynamic forces play a major role in driving DNA in microfluidic channels and causing DNA extension, such forces are screened when channel topography size approaches molecular dimensions. Applying an external electric field provides a controlled method to drive DNA. A linear relationship has been demonstrated between the translocation velocity of DNA and the external field (Menard, L. D. & Ramsey, J. M., *Anal. Chem.* 85, 1146-1153 (2013)), where DNA velocity was higher in wider channels. DNA mobility estimation showed a strong effect of external force compared to physical confinement. Nonetheless, the presence of a post structure ahead of nano-channels would alter the electric field distribution.

Figure 5:
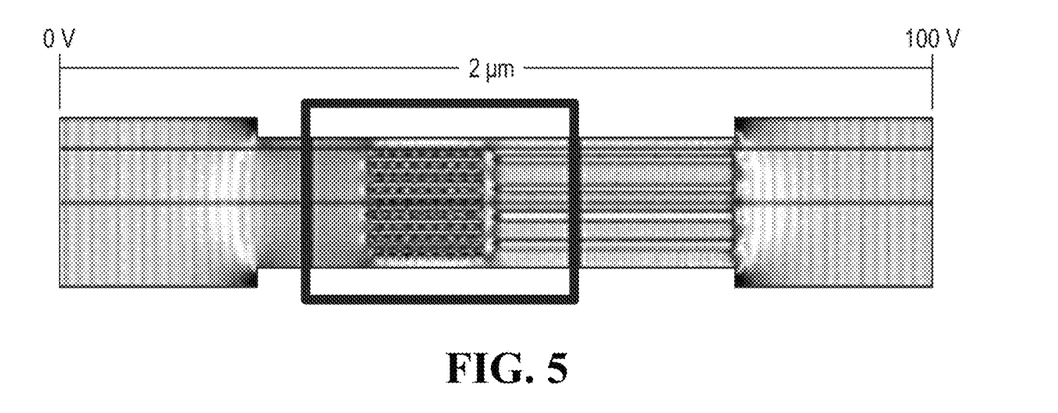
FIG. 5 is an illustration of finite element calculations of electric field distribution inside a nanoscale topography system according to one or more embodiments.
Figure 6:
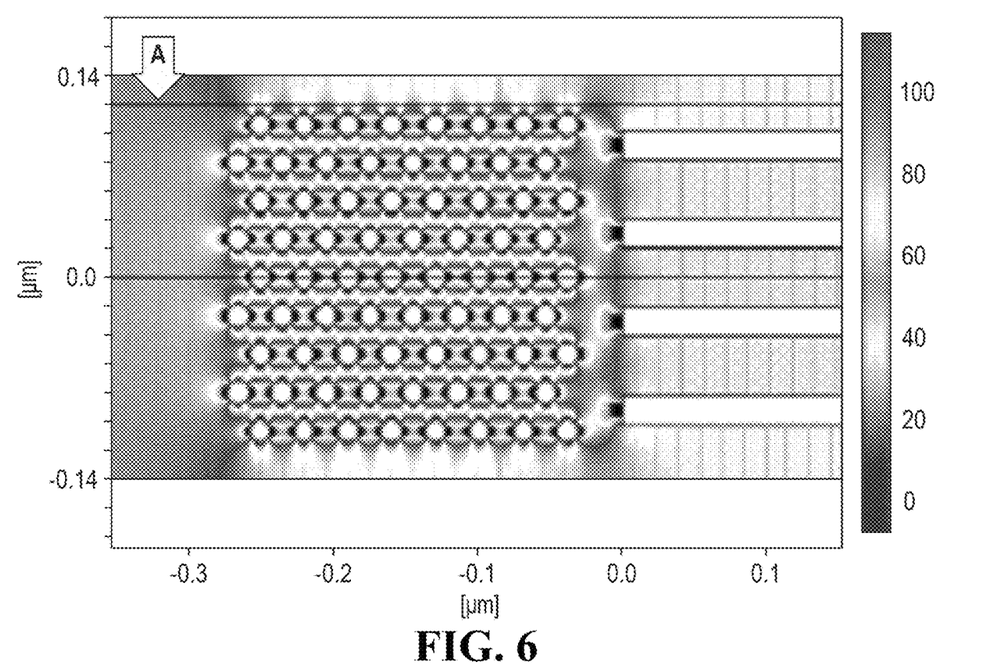
FIG. 6 is an enlarged view of the post/channel region illustrated in FIG. 5.

FIGS. 5 and 6 map the electric field for a representative post/channel topographic system (2 μm cell width) according to one or more embodiments, where the electric field drives the charged DNA molecule through the topographic pattern. As shown, electric field is relatively uniform near computational cell left and right edges where the computational electrodes are applied (100V potential difference). A nonlinear increase in field strength is observed in the vicinity of the posts 12. Furthermore, depletion regions of low electric field are located near posts 12 along the horizontal axis. These regions would have a vanishing force in driving the DNA towards the nano-channels 14.

On the other hand, concentrated fields are located along the vertical direction. There, the DNA is expected to experience a strong driving force along field lines. Stagnation points are also observed at the channel 14 entrances along the horizontal axis. The alternating magnitude of field values surrounding the post 12 would apply a non-uniform force along the molecule, causing it to stretch and unfold or unwind. Beyond the channel 14 entrance, the electric field takes a relatively constant value inside the nano-channel 14 resulting in a continuous drift of DNA towards channel 14 exit. DNA drift speed can be determined by field magnitude to allow suitable measuring time by the sensing electrode.

Figure 7:
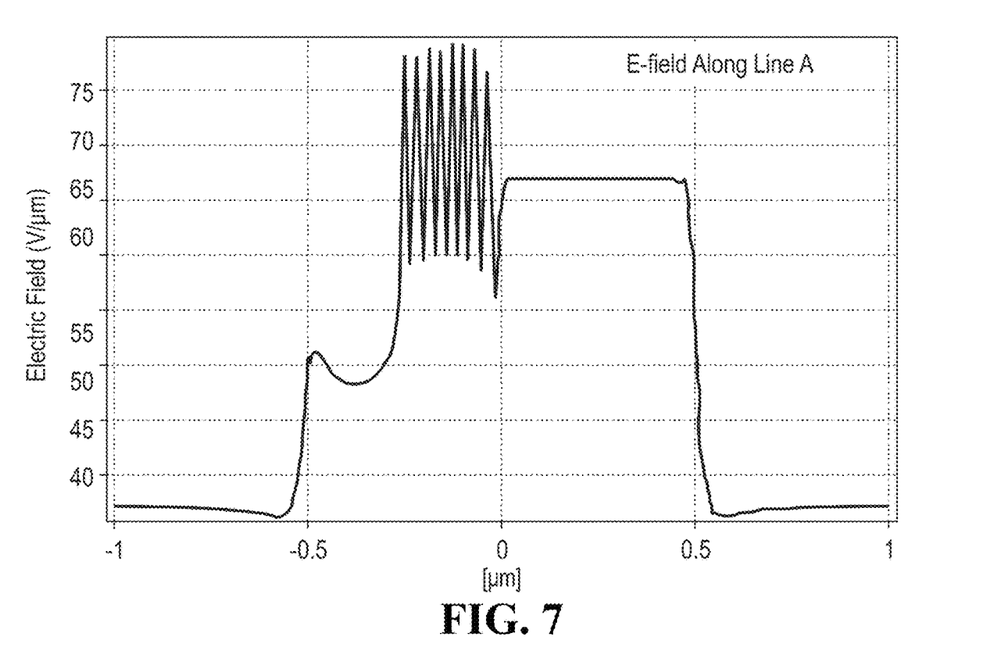
FIG. 7 is a graph of electric field as a function of distance along the nanoscale topography system of FIGS. 5 and 6.

FIG. 7 is a graph of the electric field as a function of distance along line A in FIG. 6. Electric field localization is caused by the post structure where large field magnitude is observed in the vertical direction. Relatively uniform field magnitude is present inside the nanochannels as shown in the section along line A.

Examples

Embodiments disclosed herein will now be described in more detail by way of examples thereof. It should be noted however that the disclosure is not limited to these examples.

Template Fabrication

A summary of the fabrication process is given, wherein the protocol was followed according to that described in Cheng, L. C. et al., *Nano Lett.* 18, 4360-4369 (2018); Bai, W. et al., *Nano Lett.* 150925084648002 (2015); and Cheng, J. Y et al., *Appl. Phys. Lett.* 81, 3657-3659 (2002).

Antireflective coating (ARC), AZ® BARLi® (Merck KGaA), was first spin coated on a pre-patterned substrate with sensing electrodes and then baked on a hot plate at 175° C. for 60 s to induce cross-linking. Then 20 nm $SiO_2$ was deposited by electron beam evaporation. A 200 nm photoresist (PFI 88; Sumitomo Chemical Advanced Technologies) was spin coated on top of the $SiO_2$ layer and baked on a hot plate at 90° C. for 60 seconds. The sample was exposed by an interference pattern that was generated from a 2-beam coherent laser for several minutes using a Lloyds mirror system. A post-exposure development was used to produce the photoresist grating. Then $CF_4$ plasma etching transferred the photoresist pattern into the $SiO_2$ layer and an $O_2$ plasma transferred the pattern into the ARC layer to make stable trenches to guide the self-assembly of BCPs.

Fabrication of Topographic Pattern

The fabrication steps to create topographic pattern for DNA sequencing are provided below. The fabrication sequence of steps follows that in Tavakkoli K. G., A. et al., *Nat. Commun.* 7, 1-10 (2016).

Cylindrical Domains

Surface Functionalization

To apply a PS brush (majority block), a 1 wt % solution of 1.2 kg $mol^{-1}$ hydroxyl-terminated PS (Polymer Source, Inc.) in propylene glycol monomethyl ether acetate was spin coated at 3000 r.p.m. for 30 s. Substrates were thermally annealed at 170° C. for 15 h in a vacuum oven (20 mtorr), then submerged in a bath of room-temperature toluene for 15 min, and rinsed with toluene to remove any ungrafted brush polymer.

Spin Coating

For cylinder forming PS-b-PDMS polymers, a 45.5 kg $mol^{-1}$ weight polymer ($f_{PDMS}$=32%, PDI (poly dispersity index) ~1.09) was dissolved 2 wt % in propylene glycol monomethyl ether acetate for spin coating. The equilibrium domain spacing of such molecular weight is ~30 nm. Dissolved BCPs were spin coated on the patterned substrate to a thickness which resulted in a monolayer of in-plane cylinders.

Annealing

Annealing can be achieved either thermally by placing the sample in a vacuum furnace for 16 hours at 150° C., or solvent annealing in an atmosphere of solvents. In particular, BCP was annealed in a capped glass beaker filled with 2 ml of toluene for 5-6 h, and then immediately quenched in ambient air to freeze-in the annealed structure.

Etching

Reactive-ion etching (RIE) was used to remove the PDMS top-coat and PS matrix of the BCP monolayer to leave behind oxidized, in-plane PDMS cylinders. In particular, 5 s of $CF_4$ (50 W, 15 mTorr) was used to remove the layer of PDMS that forms at the top of the BCP film, and 22 s of $O_2$ (90 W, 6 mTorr) was used to remove the PS matrix.

Spherical Domains

In order to position the posts in the vicinity of the in-plane cylinders, a photoresist is applied and patterned to cover a section of the trench and in-plane cylinders. Cylindrical domains occupying the location of posts are removed using $CF_4$.

Spin Coating

BCP fabrication steps, similar to that of cylindrical BCP, are employed to create hexagonal spherical domains including surface functionalization (Gadelrab, K. R. et al., *Nano Lett.* 18, 3766-3772 (2018)). In particular, PS-b-PDMS (minority volume fraction $f_{PDMS}$=16.5%, molecular weight 51.5 kg/mol, PDI=1.04, 1 wt % in PGMEA) was spin-coated to a thickness of 38 nm.

Annealing

The sample was annealed in a chamber of a mixed solvent of toluene and -heptane (5:1 in volume ratio) for 30 s at room temperature, followed by a thermal quenching at 60° C. for 5 s. The samples were then removed in a few seconds from the annealing chamber.

Etching

After annealing, a reactive-ion etching process of 5 s $CF_4$ (50 W, 15 mTorr) followed by 22 s of $O_2$ (90 W, 6 mTorr) was used to remove the surface coating PDMS layer and the PS matrix, and to subsequently oxidize the PDMS block into amorphous silica.

The combined structure of in-plane cylinders and hexagonal spheres is transferred to the silicon substrate using RIE. The BCP silica domains can be removed using $CF_4$ exposure.

While exemplary embodiments are described above, it is not intended that these embodiments describe all possible forms of the invention. Rather, the words used in the specification are words of description rather than limitation, and it is understood that various changes may be made without departing from the spirit and scope of the invention. Additionally, the features of various implementing embodiments may be combined to form further embodiments of the invention.

What is claimed is:

1. A nanoscale topography system for inducing unfolding of a DNA molecule for sequencing, the system comprising:
   a substrate;
   trench walls on the substrate which define a trench therebetween;
   cylindrical domains between the trench walls which are self-assembled from a layer of a block copolymer (BCP) deposited in the trench; and
   spherical domains between the trench walls and adjacent the cylindrical domains, the spherical domains self-assembled from a subsequent layer of the BCP deposited in a vacant region in the trench formed by removing a first portion of the cylindrical domains,
   wherein the self-assembled spherical domains form uniformly spaced, staggered post structures for unfolding the DNA molecule and the self-assembled cylindrical domains form parallel channel structures adjacent the post structures and parallel to the trench walls for entry of the DNA molecule for sequencing, wherein a spacing between the post structures and a width between the channel structures is of the same nanoscale order of magnitude.

2. The system of claim 1, wherein the BCP comprises polystyrene-b-polydimethylsiloxane (PS-b-PDMS).

3. The system of claim 1, wherein at least one of the trench and the trench walls includes surface functionalization to control positioning and orientation of the cylindrical and spherical domains, wherein surface functionalization is preferential to a majority block of the BCP.

4. The system of claim 1, wherein the substrate includes sensing electrodes.

5. The system of claim 1, wherein the spacing between the post structures and the width between the channel structures is approximately 10 nm.

6. A method of fabricating a nanoscale topography system for inducing unfolding of a DNA molecule for sequencing, the method comprising:
   providing a substrate;
   creating trench walls on the substrate which define a trench therebetween;
   depositing a layer of a block copolymer (BCP) in the trench and forming cylindrical domains by self-assembly of the BCP between the trench walls;
   removing a first portion of the cylindrical domains to create a vacant region in the trench; and
   depositing a subsequent layer of the BCP in the vacant region and forming spherical domains by self-assembly of the BCP between the trench walls adjacent a second portion of the cylindrical domains,
   wherein the self-assembled spherical domains form uniformly spaced, staggered post structures for unfolding the DNA molecule and the self-assembled cylindrical domains form parallel channel structures adjacent the post structures and parallel to the trench walls for entry of the DNA molecule for sequencing, wherein a spacing between the post structures and a width between the channel structures is of the same nanoscale order of magnitude.

7. The method of claim 6, wherein the BCP comprises polystyrene-b-polydimethylsiloxane (PS-b-PDMS).

8. The method of claim 6, wherein the cylindrical domains include a plurality of in-plane cylinders.

9. The method of claim 6, wherein creating the trench walls includes depositing an antireflective coating (ARC) layer on the substrate, depositing a silica layer on the ARC layer, and depositing a photoresist layer on the silica layer.

10. The method of claim 9, wherein creating the trench walls further includes producing a photoresist grating, and removing the silica layer and the ARC layer.

11. The method of claim 6, further comprising providing surface functionalization of at least one of the trench and the trench walls to control positioning and orientation of the cylindrical and spherical domains, wherein surface functionalization is preferential to a majority block of the BCP.

12. The method of claim 6, wherein forming the cylindrical domains includes annealing the layer of the BCP to facilitate self-assembly, and etching the layer of the BCP to reveal the cylindrical domains.

13. The method of claim 6, wherein removing the first portion of the cylindrical domains includes depositing a photoresist to cover the second portion of the cylindrical domains and removing the first portion of the cylindrical domains via etching.

14. The method of claim 6, wherein forming the spherical domains includes annealing the subsequent layer of the BCP to facilitate self-assembly, and etching the subsequent layer of the BCP to reveal the spherical domains.

15. The method of claim 6, further comprising transferring a combined structure of the cylindrical domains and the spherical domains to the substrate.

16. The method of claim 6, wherein the spacing between the post structures and the width between the channel structures is approximately 10 nm.

17. A method of fabricating a nanoscale topography system for inducing unfolding of a DNA molecule for sequencing, the method comprising:
   providing a substrate;
   creating trench walls on the substrate which define a trench therebetween;
   depositing a layer of a block copolymer (BCP) in the trench and forming cylindrical domains by self-assembly of the BCP between the trench walls, wherein the BCP comprises polystyrene-b-polydimethylsiloxane (PS-b-PDMS);
   removing a first portion of the cylindrical domains to create a vacant region in the trench;
   depositing a subsequent layer of the BCP in the vacant region and forming spherical domains by self-assembly of the BCP between the trench walls adjacent a second portion of the cylindrical domains; and
   providing surface functionalization of at least one of the trench and the trench walls to control positioning and orientation of the cylindrical and spherical domains, wherein surface functionalization is preferential to a majority block of the BCP, wherein the self-assembled spherical domains form uniformly spaced, staggered post structures for unfolding the DNA molecule and the cylindrical domains form parallel channel structures adjacent the post structures and parallel to the trench walls for entry of the DNA molecule for sequencing, wherein a spacing between the post structures and a width between the channel structures is of the same nanoscale order of magnitude.

18. The method of claim 17, wherein removing the first portion of the cylindrical domains includes depositing a photoresist to cover the second portion of the cylindrical domains and removing the first portion of the cylindrical domains via etching.

19. The method of claim 17, wherein forming the cylindrical domains includes annealing the layer of the BCP to facilitate self-assembly and etching the layer of the BCP to reveal the cylindrical domains, and wherein forming the spherical domains includes annealing the subsequent layer of the BCP to facilitate self-assembly and etching the subsequent layer of the BCP to reveal the spherical domains.

20. The method of claim 19, wherein etching the layer of the BCP includes removing a PDMS top coat and a PS matrix of the layer to leave behind a plurality of in-plane PDMS cylinders, and etching the subsequent layer of the BCP includes removing a PDMS top coat and a PS matrix of the subsequent layer to leave behind a plurality of PDMS spherical domains.

* * * * *